(12) United States Patent
Zhu

(10) Patent No.: US 7,666,989 B2
(45) Date of Patent: Feb. 23, 2010

(54) RECOMBINANT PROTEIN HAVING AN ANTI-CANCER EFFECT, ITS ENCODING GENE AND USES THEREOF

(75) Inventor: Bing Zhu, Beijing (CN)

(73) Assignee: Beijing Sunbio Biotech Co., Ltd., Beijing (CN)

( * ) Notice: Subject to any disclaimer, the term of this patent is extended or adjusted under 35 U.S.C. 154(b) by 389 days.

(21) Appl. No.: 10/577,535

(22) PCT Filed: Nov. 3, 2003

(86) PCT No.: PCT/CN03/00928

§ 371 (c)(1),
(2), (4) Date: Apr. 27, 2006

(87) PCT Pub. No.: WO2005/042744

PCT Pub. Date: May 12, 2005

(65) Prior Publication Data

US 2008/0280821 A1    Nov. 13, 2008

(51) Int. Cl.
    *C07K 14/00* (2006.01)
(52) U.S. Cl. ..................................................... 530/350
(58) Field of Classification Search .................. None
    See application file for complete search history.

(56) References Cited

U.S. PATENT DOCUMENTS 6,284,236 B1 * 9/2001 Wiley et al. ................. 424/85.1
2002/0128438 A1 9/2002 Seol et al.

FOREIGN PATENT DOCUMENTS

| KR | 10-2001-0019100 | 3/2001 |
| KR | 2002-0004495 | 1/2002 |
| WO | WO 97/01633 | 1/1997 |
| WO | WO 01/79495 A1 | 10/2001 |

OTHER PUBLICATIONS

Pitti et al, Journal of Biological Chemistry, vol. 271, No. 22, Issue of May 31, 1996 pp. 12687-12690.*

Wiley et al., "Identification and Characterization of a New Member of the TNF Family that Induces Apoptosis", Immunity 3:673-682, 1995.

Greil et al., *Tracking death dealing by Fas and Trail in lymphatic neoplastic disorders: pathways, targets, and therapeutic tools*, Journal of Leukocyte Biology, vol. 74, pp. 311-330 (Sep. 2003).

LeBlanc and Ashkenazi, *Apo2L/Trail and its death and decoy receptors*, Cell Death and Differentiation, pp. 66-75 (2003).

Walczak et al., *Tumoricidal activity of tumor necrosis factor-related apoptosis-inducing ligand* in vivo, Nature Medicine, vol. 5, No. 2, pp. 157-163 (Feb. 1999).

* cited by examiner

*Primary Examiner*—Misook Yu
(74) *Attorney, Agent, or Firm*—Scully, Scott, Murphy & Presser, P.C.

(57) ABSTRACT

The present invention discloses a recombinant protein having an anti-cancer effect, its encoding gene and uses thereof. The recombinant protein having an anti-cancer effect provided by the present invention is one selected from the group consisting of: 1) a protein having the amino acid sequence of SEQ ID No:2 shown in the sequence listing; 2) a protein derived from SEQ ID No:2, which has a sequence homology of more than 90% with SEQ ID No:2 and which has the same activity as that of SEQ ID No:2; 3) a protein derived from SEQ ID No:2, which is obtained by adding or deleting 15 or less amino acid residues at the N-terminus of the amino acid sequence of SEQ ID No:2, and which has the same activity as that of SEQ ID No:2; 4) a protein derived from SEQ ID No:2, which is obtained by adding or deleting 15 or less amino acid residues at the C-terminus of the amino acid sequence of SEQ ID No:2, and which has the same activity as that of SEQ ID No:2; 5) a protein derived from SEQ ID No:2, which is obtained by substitution, deletion, or addition of one or several amino acid residues in the amino acid sequence of SEQ ID No:2, and which has the same activity as that of SEQ ID No:2. The medicament containing above recombinant protein as active component has significant selective inhibitory effect on tumor cells, and does not induce apoptosis of normal tissue cells, and has important applicable value.

7 Claims, 4 Drawing Sheets

SEQUENCE LISTING

<160> NUMBER OF SEQ ID NOS: 2

<210> SEQ ID NO 1
<211> LENGTH: 501
<212> TYPE: DNA
<213> ORGANISM: Artificial Sequence
<220> FEATURE:
<223> OTHER INFORMATION: Synthetically generated oligonucleotide

<400> SEQUENCE: 1

```
acattgtctt ctccaaactc caagaatgaa aaggctctgg gccgcaaaat aaactcctgg      60
gaatcatcaa ggagtgggca ttcattcctg agcaacttgc acttgaggaa tggtgaactg     120
gtcatccatg aaaaagggtt ttactacatc tattcccaaa catactttcg atttcaggag     180
gaaataaaag aaaacacaaa gaacgacaaa caaatggtcc aatatattta caaatacaca     240
agttatcctg accctatatt gttgatgaaa agtgctagaa atagttgttg gtctaaagat     300
gcagaatatg gactctattc catctatcaa gggggaatat ttgagcttaa ggaaaatgac     360 agaattttg tttctgtaac aaatgagcac ttgatagaca tggaccatga agccagtttt     420
tttggggcct ttttagttgg cggtggtggt ggtggtgtag cagctcacat aactgggacc     480
agaggaagaa gcaacacata a                                                501
```

<210> SEQ ID NO 2
<211> LENGTH: 166
<212> TYPE: PRT
<213> ORGANISM: Artificial Sequence
<220> FEATURE:
<223> OTHER INFORMATION: Synthetically generated peptide

<400> SEQUENCE: 2

```
Thr Leu Ser Ser Pro Asn Ser Lys Asn Glu Lys Ala Leu Gly Arg Lys
 1               5                  10                  15

Ile Asn Ser Trp Glu Ser Ser Arg Ser Gly His Ser Phe Leu Ser Asn
            20                  25                  30

Leu His Leu Arg Asn Gly Glu Leu Val Ile His Glu Lys Gly Phe Tyr
        35                  40                  45
```

-continued

```
Tyr Ile Tyr Ser Gln Thr Tyr Phe Arg Phe Gln Glu Glu Ile Lys Glu
    50                  55                  60

Asn Thr Lys Asn Asp Lys Gln Met Val Gln Tyr Ile Tyr Lys Tyr Thr
65              70                  75                      80

Ser Tyr Pro Asp Pro Ile Leu Leu Met Lys Ser Ala Arg Asn Ser Cys
            85                  90                  95

Trp Ser Lys Asp Ala Glu Tyr Gly Leu Tyr Ser Ile Tyr Gln Gly Gly
            100                 105                 110

Ile Phe Glu Leu Lys Glu Asn Asp Arg Ile Phe Val Ser Val Thr Asn
        115                 120                 125

Glu His Leu Ile Asp Met Asp His Glu Ala Ser Phe Phe Gly Ala Phe
        130                 135                 140

Leu Val Gly Gly Gly Gly Gly Val Ala Ala His Ile Thr Gly Thr
145                 150                 155                 160

Arg Gly Arg Ser Asn Thr
                165
```

RECOMBINANT PROTEIN HAVING AN ANTI-CANCER EFFECT, ITS ENCODING GENE AND USES THEREOF

CROSS-REFERENCE TO RELATED APPLICATIONS

This application is the National Stage of International Application No. PCT/CN2003/000928, filed on Nov. 3, 2003.

FIELD OF THE INVENTION

The present invention pertains to the field of genetic engineering and pharmacology. The present invention relates to a recombinant protein, its encoding gene, and a genetic engineering medicament containing said recombinant protein as the active ingredient. In particular, the present invention relates to a recombinant protein having an anti-cancer effect, its encoding gene, and a medicament for the treatment of cancers containing said recombinant protein as the active ingredient.

BACKGROUND OF THE INVENTION

During evolution, mammalians establish gradually a set of signaling mechanisms for apoptosis which can induce programmed death of individual cells. The underlying theory is that ligands of lethal cells interact with the death receptors on cell surfaces, which induces apoptosis of cells. Such beneficial apoptosis plays a critical physiological role in the elimination of activated lymphocytes at the end of an immune response and in the elimination of virus-infected cells and oncogenically transformed cells. The examples thereof include the interaction between TNF and receptor TNFR, and the interaction between FasL and receptor Fas/Apo1/CD95.

The activated death receptors are directly involved in the cascade reactions of cell apoptosis. They can induce the apoptosis of various cancer cells, and are potential anti-cancer factors. Although TNF and FasL can induce the apoptosis of cancer cells, they cause severe toxic and side effects in anti-cancer therapy. Injection of TNF can lead to fatal inflammatory responses similar to septic shocks. This response is mainly mediated by NF-κB, a pre-transcriptional factor, which is located in vascular endothelial cells and macrophages and which is activated by TNF. Anti-Fas antibody can induce a Fas-dependent cell apoptosis in liver tissues, and cause fatal liver damages.

Wiley et al. discovered TNF-related apoptosis-inducing ligand (TRAIL) based on the sequence identity with TNF and FasL in 1995. TRAIL can induce apoptosis by interacting with death receptor DR4 or DR5. Unlike TNF and FasL, the mRNA of TRAIL is constitutively expressed in many normal human tissues. This indicates a physiological mechanism by which TRAIL induces apoptosis of cancer cells while sparing normal cells. These mechanisms include: expression of inhibitory receptors, ability of competing with DR4 and DR5 for binding to ligands, ability of TRAIL to interact with three receptors DcR1, DcR2 and DPG. Therefore, the toxicity of TRAIL is less than TNF and FasL.

SUMMARY OF THE INVENTION

The object of the present invention is to provide a recombinant protein with an anti-cancer effect, and a medicament for effectively treating cancers which contains the recombinant protein as the active ingredient.

The recombinant protein having an anti-cancer effect according to the present invention is one selected from the group consisting of:

1) a protein having the amino acid sequence of SEQ ID No:2 shown in the sequence listing;

2) a protein derived from SEQ ID No:2, which has a sequence homology of more than 90% with SEQ ID No:2 and which has the same activity as that of SEQ ID No:2;

3) a protein derived from SEQ ID No:2, which is obtained by adding or deleting 15 or less amino acid residues at the N-terminus of the amino acid sequence of SEQ ID No:2, and which has the same activity as that of SEQ ID No:2;

4) a protein derived from SEQ ID No:2, which is obtained by adding or deleting 15 or less amino acid residues at the C-terminus of the amino acid sequence of SEQ ID No:2, and which has the same activity as that of SEQ ID No:2;

5) a protein derived from SEQ ID No:2, which is obtained by substitution, deletion, or addition of one or several amino acid residues in the amino acid sequence of SEQ ID No:2, and which has the same activity as that of SEQ ID No:2.

The protein of SEQ ID No:2 as shown in the sequence listing is human recombinant circularly permuted TRAIL (CPT), which consists of 166 amino acid residues.

The active ingredient of the medicament for treating cancers provided by the present invention (CPT) is one of the aforementioned proteins.

If desired, one or more pharmaceutically acceptable carriers may be added into the above medicament. The carrier includes a diluent, excipient, filler, binder, wetter, disintegrant, absorption enhancer, surfactant, adsorbent carrier, lubricant commonly used in the field of pharmaceuticals. If necessary, a flavoring, sweetener and the like may also be added.

The medicament according to the present invention may be formulated into various forms, including injectable solution, tablet, powder, granule, capsule, orally administered fluid, ointment and cream, etc. Any of the aforementioned dosage forms of the medicament may be prepared by routine methods in the field of pharmaceuticals.

The encoding sequence of the active ingredient (protein) of the medicament for treating cancers (CPT) provided by the present invention is one selected from the group consisting of:

1) SEQ ID No:1 shown in the sequence listing;

2) a polynucleotide encoding the amino acid sequence of SEQ ID No:2 shown in the sequence listing;

3) a DNA sequence which has more than 90% sequence homology with the DNA sequence defined by SEQ ID No:1 shown in the sequence listing and which encodes a protein having the same activity as that of a protein encoded by SEQ ID No:1;

4) a DNA sequence encoding a protein derived from SEQ ID No:2, wherein said protein derived from SEQ ID No:2 is obtained by adding or deleting 15 or less amino acid residues at the N-terminus of the amino acid sequence of SEQ ID No:2, and has the same activity as that of SEQ ID No:2;

5) a DNA sequence encoding a protein derived from SEQ ID No:2, wherein said protein derived from SEQ ID No:2 is obtained by adding or deleting 15 or less amino acid residues at the C-terminus of the amino acid sequence of SEQ ID No:2, and has the same activity as that of SEQ ID No:2;

6) a DNA sequence encoding a protein derived from SEQ ID No:2, wherein said protein derived from SEQ ID No:2 is obtained by substitution, deletion, or addition of one or several amino acid residues in the amino acid sequence of SEQ ID No:2, and has the same activity as that of SEQ ID No:2.

SEQ ID No:1 in the sequence listing consists of 501 base pairs. The reading frame thereof is nucleotides 1-498 from the 5'-end.

Expression vectors and cell lines (such as *Escherichia coli* and yeast expression systems, etc.) containing the gene of the present invention are within the scope of the present invention.

BRIEF DESCRIPTION OF THE FIGURES

FIG. 4-1 to FIG. 4-6 show the histopathological sections of human lung cancer NCI-H460 under different treatment conditions (HE staining×100).

FIG. 5 shows the tumor sizes of human lung cancer NCI-H460 under different treatment conditions.

FIG. 6 shows the tumor volume curves of human-colon cancer COLO 205 under different treatment conditions.

FIG. 7-1 to FIG. 7-5 show BALB/c-nu nude mice which were inoculated with human colon cancer COLO 205 followed by different treatments.

BEST MODES FOR CARRYING OUT THE INVENTION

Example 1

Figure 1:
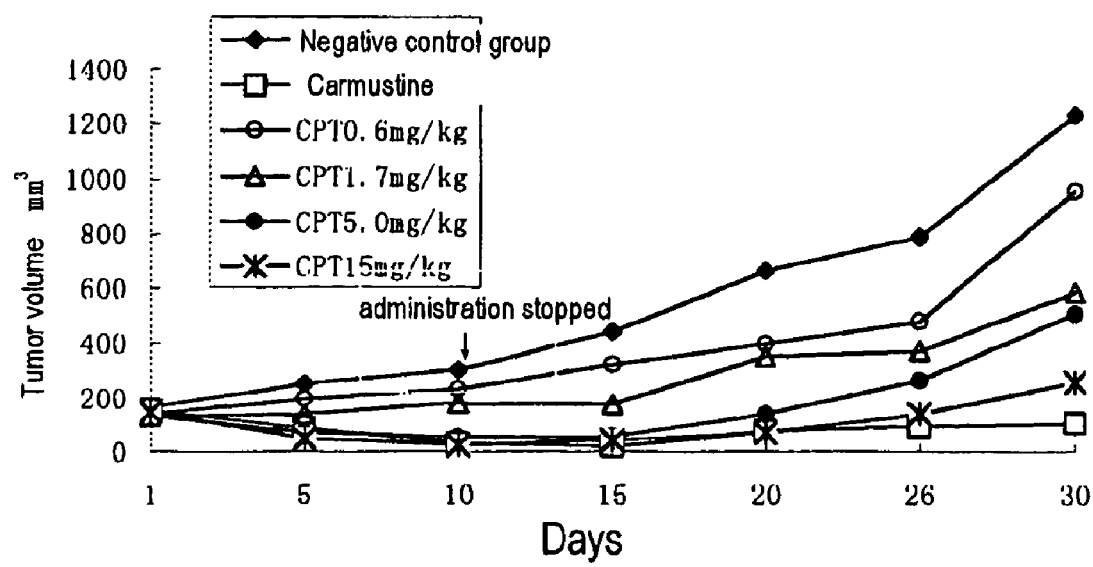
FIG. 1 shows the tumor volume curves of human glioma U251 under different treatment conditions.

Construction and Expression of the Encoding Gene of Recombinant Human Circularly Permuted TRAIL The gene sequence encoding amino acid residues at positions 121-281 of human TRAIL was obtained from human spleen cDNA library. The gene encoding amino acid residues at positions 135-281 of human TRAIL was generated by routine PCR method using human TRAIL gene as the template. Then the DNA sequence encoding the amino acid residues 122-135 of TRAIL was linked to 3'-end of the DNA sequence encoding the amino acid residues at positions 135-281 of TRAIL by PCR method. A DNA sequence encoding five glycine residues was inserted between the DNA sequence encoding the amino acid residues 135-281 of TRAIL and the DNA sequence encoding the amino acid residues 122-135 of TRAIL. The flexibility of glycine can facilitate proper protein folding. The CPT encoding gene thus obtained was ligated into vector plasmid pet28b (or other vector plasmid) using NcoI and BamHI, resulting in an expression plasmid. The DNA sequence thereof was confirmed to be correct by sequencing.

The expression plasmid was transformed into *E. coli* strain BL21 (DE3). The transformed *E. Coli* was inoculated into 10 ml of LB liquid medium containing 20 μg/ml kanamycin. The cells were incubated on a shaker at 37° C. for 12 hours. Then 10 ml of the culture was inoculated into 1 L of LB liquid medium containing 20 μg/ml kanamycin and further culture was conducted. When $OD_{600}$ reached 0.6, 0.2 ml of 1 M IPTG was added into 1 L of culture to induce protein expression. The cells were harvested via centrifugation after three hours of induction. The pellet was suspended in 100 ml buffer containing 100 mM Tris (pH 7.9) and 150 mM NaCl.

The cells were lysed by sonication at 4° C. and were centrifuged at 15,000 rpm using a Beckman JA20 rotor. Since the expressed protein is capable of binding with a metal chelate resin, it may be purified by a metal-chelating chromatography. After centrifugation, the supernatant was pumped into an immobilized $Ni^{2+}$-chelate chromatography column. The column was washed by a buffer containing 50 mM Tris (pH 7.9), 0.5 M NaCl and 50 mM imidazole to remove contaminating proteins contained therein. The bound protein was then eluted by a buffer containing 50 mM Tris (pH 7.9), 0.5 M NaCl and 200 mM imidazole. The eluted protein was dialyzed against PBS buffer.

Finally, the protein was purified by an ion exchange column and a gel filtration column Superdex 200 (Pharmacia) mounted in an AKTA HPLC system (Pharmacia). Analysis of the protein indicated that the protein thus obtained had an amino acid sequence of SEQ ID No:2, which is the anti-cancer medicament of the present invention. The end product was a white powder and was water soluble.

Example 2

Determination of the Cytotoxic Effects of the Medicament of the Present Invention on Cancer Cells Using Tetrazolium Reduction Method (MTT)

Reagents: RPMI1640 is from GIBCO; MTT is from Bebco. Fetal bovine serum is purchased from Hangzhou SiJi-Qing Bioengineering Material Co. Ltd. (P. R. China).

Cell lines: COLO 205 (human colon cancer cell), NCI-H460 (human lung cancer cell), RPMI 8226 (human multiple myeloma cell), U251 (human brain glioma cell) are from ATCC, USA. HL-60 (human promyelocytic leukemia cell), MDA-MB-231, MDA-MB-435 (human breast cancer cell), SCLC (human small-cell lung cancer cell), H125 (human lung cancer cell) and PC-3 (human pancreas cancer cell).

The well-grown tumor cells were collected to prepare a cell suspension ($1 \times 10^4$/ml) with RPMI 1640 medium containing 10% fetal bovine serum. The cell suspension was inoculated into a 96-well plate, 100 μL (containing 1000 tumor cells) per well. The plate was cultured in a 5% $CO_2$ incubator at 37° C. for 24 hours, followed by addition of medicament.

A blank control and a positive control using 5-fluorouracil or adriamycin are employed in the experiment. The CPT samples have five concentrations, three parallel wells for each concentration. The cells were cultured in an incubator with 5% $CO_2$ at 37° C. for 4 days. Then the culture medium was removed and 100 μL MTT solution (0.4 mg/ml in RPMI 1640) was added to each well. The plate was incubated at 37° C. for four additional hours.

The supernatant was discarded. 150 μl DMSO was added into each well in order to solubilize Fomazan granulates. After gently shaking, the OD values were measured by a BIORAD 550 enzyme analyzer, with the detection wavelength being 540 nm and the reference wavelength being 450 nm.

Dose-response curves were generated by plotting with the cell inhibition rates and different concentrations of medicament, and the half inhibitory concentrations ($IC_{50}$) were calculated. The results were shown in Table 1. It can be seen that CPT has an extremely strong killing effect on human tumor cells U251, COLO205, NCI-H460, MDA-MB-435, wherein $IC_{50} < 0.01$ μg/ml. CPT also has a very strong killing effect on HL-60, MDA-MB-231, PC-3 and HL125 cells, wherein $IC_{50} < 0.1$ μg/ml. CPT has a good effect on RPMI 8226 cell, wherein $IC_{50} < 1$ μg/ml. It also shows some inhibitory effect on the growth of SCLC cell. The activity of CPT to induce apoptosis of cancer cells is six to eleven times as strong as that of wild type TRAIL.

TABLE 1

The killing effects of CPT on human tumor cell lines (x ± SD)

| Tumor cell line | IC$_{50}$ (μg/ml) | | |
|---|---|---|---|
| | CPT | Fu | Adr |
| U251 | <0.001 | 0.981 ± 0.077 | |
| COLO 205 | 0.006 ± 0 | 0.826 ± 0.051 | |
| MDA-MB-435 | 0.008 ± 0.002 | 0.199 ± 0.138 | |
| HL-60 | 0.014 ± 0.013 | | 0.006 ± 0 |
| NCI-H460 | 0.002 ± 0.001 | 0.566 ± 0.016 | |
| MDA-MB-231 | 0.043 ± 0.0131 | 0.318 ± 0.055 | |
| PC-3 | 0.067 ± 0.002 | 4.928 ± 0.753 | |
| H125 | 0.085 ± 0.006 | 0.138 ± 0.031 | |
| RPMI 8226 | 0.824 ± 0.093 | <0.1 | |
| SCLC | 10 ± 0 | 0.617 ± 0.0257 | |

Note:
FU denotes 5-fluorouracil control; Adr denotes Adriamycin control.

Example 3

The Inhibition Effects of the Medicament of the Present Invention on the Growth of Human Cancer Xenograft in Nude Mice In this example, the animals used were BALB/c-nu nude mice, 6-8 weeks old. For each experiment, all animals were of the same sex.

Tumor cell lines: human brain glioma U251, human lung cancer cell line NCI-H460, human colon cancer cell line COLO205 were inoculated from in vitro culture into nude mice subcutaneously, the tumors were subcultured and kept.

Experimental Procedures: well-grown nude mice carrying well-grown tumors were selected and sacrificed by disjointing neck vertebra. The tumors were removed aseptically and were cut into pieces having a diameter of 2-3 mm by a scalpel. The pieces were inoculated into the axilla of nude mice subcutaneously by a needle. Tumors could be found in the axilla of the animals after about 7-10 days. The length and width of tumors were measured by a vernier caliper. The animals were then grouped based their tumor sizes. Each group included seven to eight animals.

The length, width of the tumor and the body weight of the mice were measured twice per week. The tumor volume (TV) and relative tumor volume (RTV) were calculated. A graph indicating the changes of tumor size was plotted. At the end of this experiment, the tumors were taken out and weighed after the mice were sacrificed, and the inhibition rates of the medicament on tumor growth were calculated.

The formula for calculating tumor volume (TV) is: length×width$^2$÷2.

The formula for calculating relative tumor volume (RTV) is: Vt/Vo (wherein Vo is the TV value measured when the administration is started, Vt is the TV value measured after that).

T-test was used to determine the statistical difference of tumor weights, tumor volumes and RTV etc. between different groups of animal. The index used for evaluating the anti-tumor activity is the relative tumor growth rate T/C (%), the formula for which is:

$$T/C(\%) = \frac{RTV \text{ of the group receiving medicament}(T)}{RTV \text{ of the negative control}(C)} \times 100$$

The evaluation standard for efficacy:

T/C (%)>60 is ineffective;

T/C (%)≦60 and P<0.05 after statistical analysis is effective.

1. The Inhibitory Effect on Human Brain Glioma U251

The Carmustine (Renmin Pharmaceuticals, Amino Acid Inc. Tianjin, P. R. China) was used as the positive control, 40 mg/kg, administered by intraperitoneal injection for once. CPT was given to four groups at the doses of 0.6 mg/kg, 1.7 mg/kg, 5.0 mg/kg, 15.0 mg/kg respectively, administered by intraperitoneal injection. The treatment included ten injections.

Figure 2:
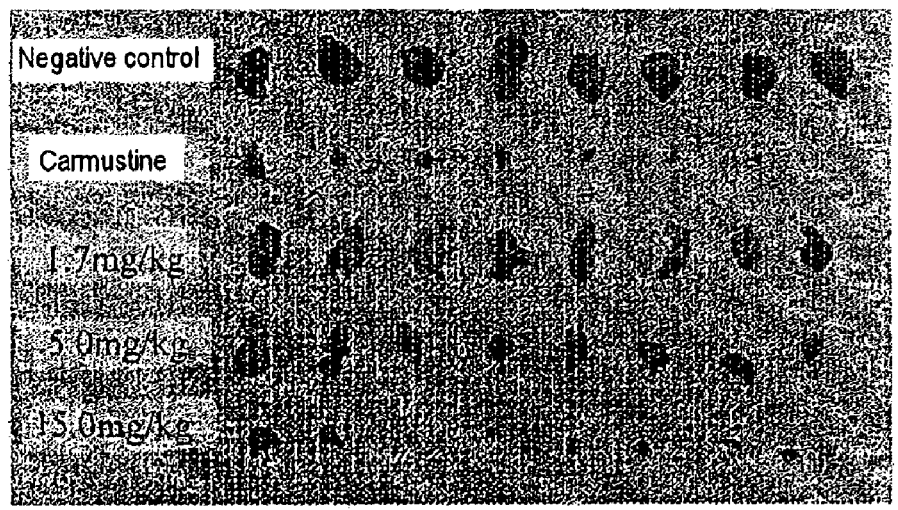
FIG. 2 shows the tumor sizes of human glioma. U251 under different treatment conditions.

The experimental results are shown in Table 1 and 2 and FIGS. 1 and 2. It can be seen that CPT exhibited a significant inhibitory effect on the growth of transplanted tumors (human brain glioma U251) in nude mice. The tumor inhibition rates calculated by weight for the four treatment groups were 30.5%, 44.5%, 64.8% and 87.5% respectively. Compared with the control group, the tumor weights of the treatment groups showed a significant or very significant statistical difference. The anti-tumor effect of CPT was significantly dose-dependent. The relative tumor growth rate T/C(%) values for the groups of 5.0 mg/kg and 15 mg/kg were <60. The relative tumor volume (RTV) for the group of 15 mg/kg was significantly different in statistics compared with that of the control group.

TABLE 2

The inhibition effect of CPT on the growth of human glioma U251 (x ± SD)

| Group | Animal number | | Body Weight (g) | | Tumor weight (g) | Inhibition rate (%) |
|---|---|---|---|---|---|---|
| | Start | End | Start | End | | |
| Negative control | 8 | 8 | 21.9 ± 1.1 | 22.3 ± 2.6 | 1.28 ± 0.50 | |
| Carmustine control | 8 | 7 | 22.8 ± 0.7 | 19.4 ± 2.1 | 0.09 ± 0.06** | 93.0 |
| CPT 0.6 mg/kg | 8 | 8 | 21.0 ± 0.8 | 21.0 ± 1.4 | 0.89 ± 0.49 | 30.5 |
| CPT 1.7 mg/kg | 8 | 8 | 21.6 ± 1.2 | 21.5 ± 2.0 | 0.71 ± 0.22* | 44.5 |
| CPT 5.0 mg/kg | 8 | 8 | 22.0 ± 1.1 | 21.9 ± 3.2 | 0.45 ± 0.26** | 64.8 |
| CPT 15 mg/kg | 8 | 8 | 21.6 ± 1.1 | 21.1 ± 1.7 | 0.16 ± 0.15** | 87.5 |

TABLE 3

The inhibition effect of CPT on the growth
of human glioma U251 (x ± SD)

| Group | Tumor volume (mm³) | | | T/C (%) |
|---|---|---|---|---|
| | Start | End | RTV | |
| Negative control | 165 ± 72 | 1238 ± 244 | 3.34 ± 2.28 | |
| Carmustine control | 153 ± 35 | 109 ± 78** | 0.54 ± 0.29** | 16.0 |
| CPT 0.6 mg/kg | 141 ± 40 | 961 ± 582 | 2.77 ± 1.97 | 82.9 |
| CPT 1.7 mg/kg | 131 ± 34 | 588 ± 215** | 2.12 ± 1.29 | 63.5 |
| CPT 5.0 mg/kg | 133 ± 57 | 510 ± 333** | 1.32 ± 1.24* | 39.5 |
| CPT 15 mg/kg | 148 ± 58 | 261 ± 238** | 0.71 ± 0.57** | 21.3 |

*$P < 0.05$
**$P < 0.01$ compared with the negative control group

2. The Inhibition Effect on Human Lung Cancer NCI-H460

Cyclophosphamide (Shanghai Hualian Pharma Inc., P. R. China) was used as the positive control, administered by intraperitoneal injection at the dose of 100 mg/kg. One additional injection was given at 80 mg/kg two weeks later. CPT was given to three treatment groups at the doses of 1.7 mg/kg, 5.0 mg/kg, 15.0 mg/kg respectively, administered by intraperitoneal injection once per day. The treatment contained a total of ten injections.

Figure 3:
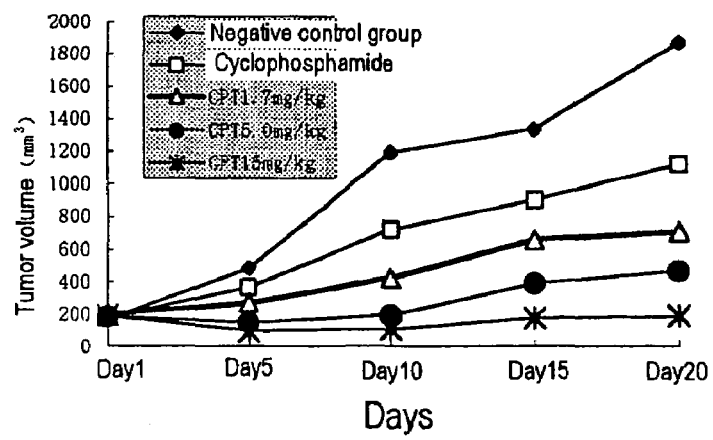
FIG. 3 shows the tumor volume curves of human lung cancer NCI-H460 under different treatment conditions.
Figures 1, 4:
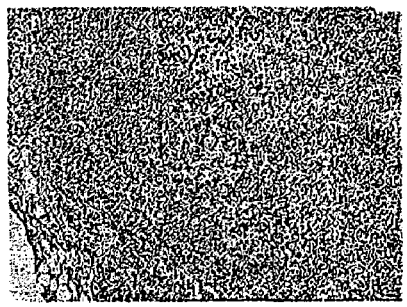
Figures 2, 4:
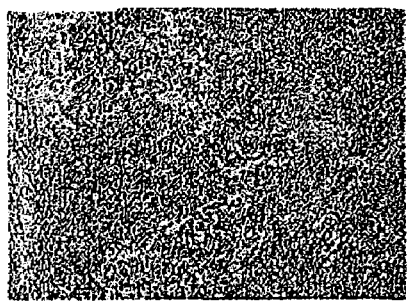
Figures 3, 4:
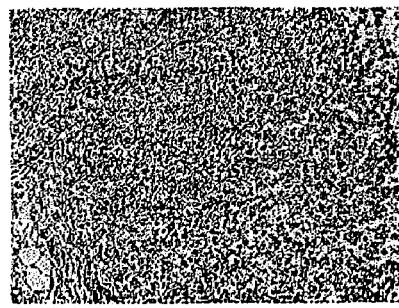
Figure 4:
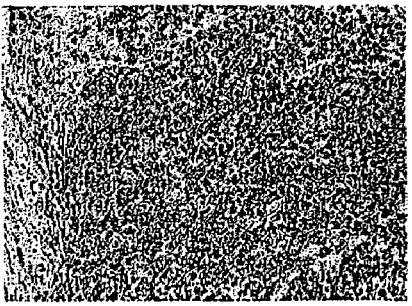
Figures 4, 5:
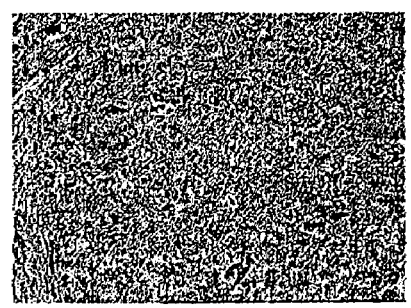

The experimental results are shown in Table 4 and 5 and FIGS. 3 and 5. It can be seen that CPT exhibited a significant inhibition effect on the growth of transplanted tumors (human lung cancer NCI-H460) in nude mice. The tumor inhibition rates calculated by weight for the three treatment groups were 52.2%, 74.5% and 87.0% respectively. Compared with the control group, the tumor weights of the treatment groups had a significant or very significant statistical difference. The relative tumor growth rate (%) values for the groups of 5.0 mg/kg and 15 mg/kg were <60; the relative tumor volumes (RTV) were significantly different in statistics compared with that of the control group.

TABLE 4

The inhibition effect of CPT on the growth of human lung cancer NCI-H460

| Group | Animal number | | Body Weight (g) | | Tumor weight (g) | Inhibition rate (%) |
|---|---|---|---|---|---|---|
| | Start | End | Start | End | | |
| Negative control | 8 | 7 | 21.4 ± 0.9 | 19.3 ± 1.0 | 1.61 ± 0.65 | |
| Cyclophosphamide control | 8 | 7 | 20.0 ± 1.3 | 16.1 ± 2.2 | 0.96 ± 0.35* | 40.4 |
| CPT 1.7 mg/kg | 8 | 7 | 20.1 ± 1.9 | 19.8 ± 1.6 | 0.77 ± 0.19** | 52.2 |
| CPT 5.0 mg/kg | 8 | 8 | 20.4 ± 1.9 | 18.5 ± 2.5 | 0.41 ± 0.28** | 74.5 |
| CPT 15 mg/kg | 8 | 8 | 20.9 ± 1.1 | 21.1 ± 1.7 | 0.21 ± 0.10** | 87.0 |

TABLE 5

The inhibition effect of CPT on the growth of human lung cancer NCI-H460

| Group | Tumor volume (mm³) | | | T/C (%) |
|---|---|---|---|---|
| | Start | End | RTV | |
| Negative control | 169 ± 58 | 1874 ± 637 | 5.98 ± 4.05 | |
| Cyclophosphamide control | 179 ± 52 | 1121 ± 434 | 3.67 ± 2.15 | 61.4 |
| CPT 1.7 mg/kg | 200 ± 103 | 706 ± 170* | 2.27 ± 1.13* | 38.0 |
| CPT 5.0 mg/kg | 187 ± 51 | 469 ± 359** | 1.49 ± 0.76** | 24.9 |
| CPT 15 mg/kg | 192 ± 63 | 189 ± 102** | 0.79 ± 0.25** | 13.2 |

*$P < 0.05$
**$P < 0.01$ compared with the negative controls.

Figures 4, 5, 6:
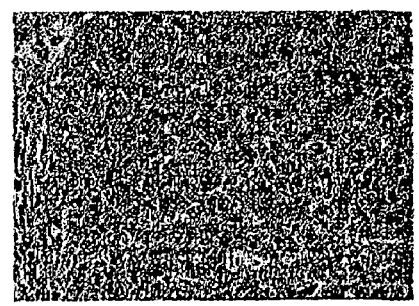
Figure 5:
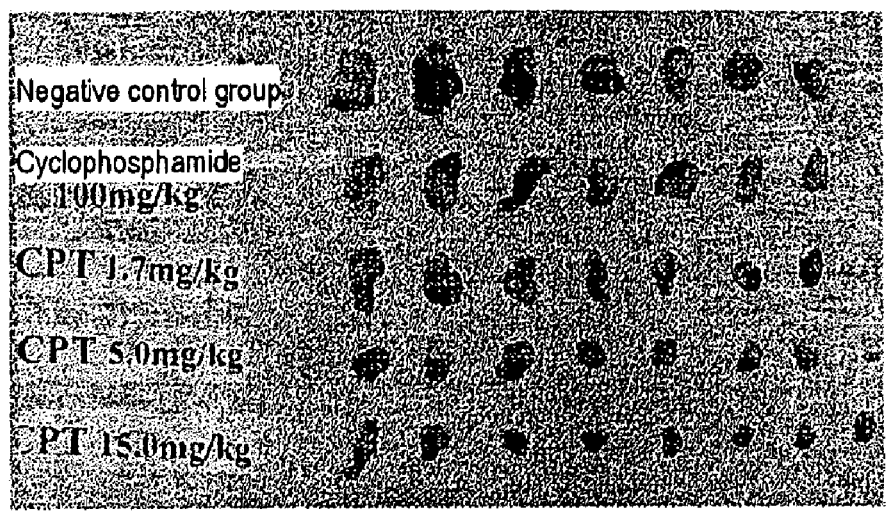
Figure 6:
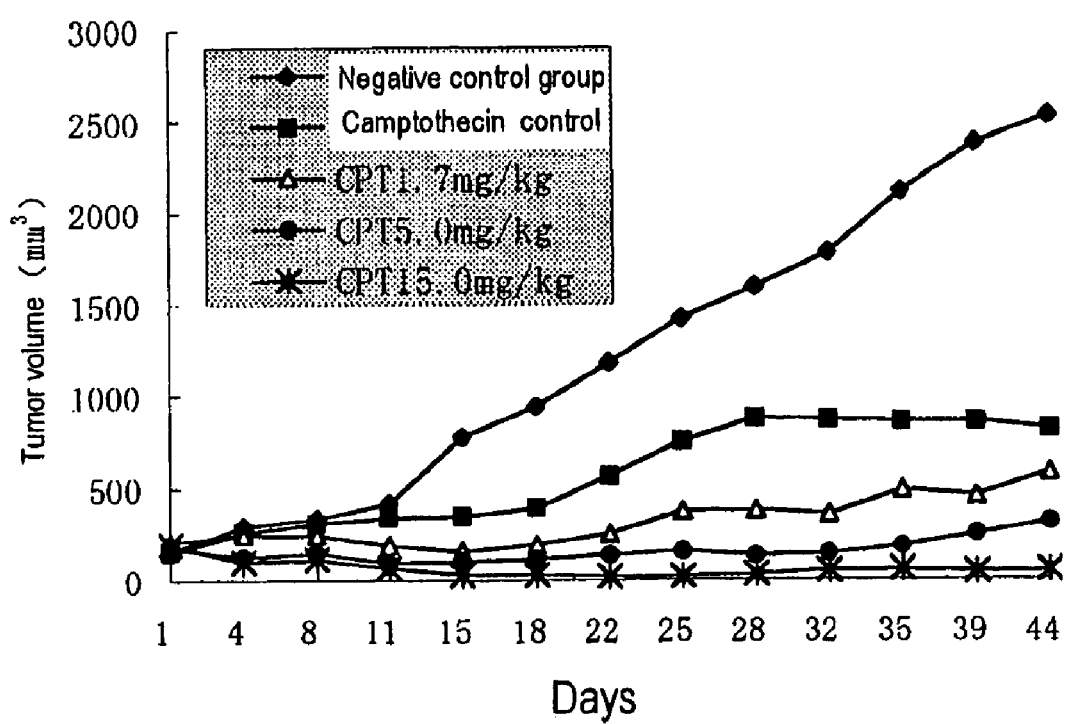

The results of histopathological tests were shown in FIG. 4-1 to FIG. 4-6. FIGS. 4-1, 4-3 and 4-5 were of negative control group. FIG. 4-1 showed that the tumor tissues diffused and were fascicle-like. There was a large liquefactive necrosis in the center of the tumor. The tumor was surrounded by thin connective tissue membrane and was poorly infiltrated by lymphocytes. FIG. 4-3 showed that the tumor cells were arranged in solid fascicle- and cord-like structures. The tumor tissue had rich capillaries and was not infiltrated by lymphocytes. FIG. 4-5 showed that the tumor cells were round or multi-angled, had large nuclei, and had little cytoplasm. The chromatin was loose, the nucleoli were apparent, and there were 2-3 nucleoli, which showed multiple signs of mitosis. FIGS. 4-2, 4-4 and 4-6 were for the group treated with 15 mg/kg CPT. FIG. 4-2 showed that the tumor tissues were solid fascicles, and sheet-like necrosis appeared in the center. There was much proliferated connective tissue in the tumor, and thin connective tissue envelope around the tumor. The tumor was poorly infiltrated by lymphocytes. FIG. 4-4 showed that the tumor cells were arranged in cord-like structures. The tumor tissue had few capillaries and had necrosis in the center. It was surrounded by connective tissue envelope and infiltrated by a few lymphocytes. FIG. 4-6 showed that the tumor cells were round or multi-angled, the nucleoli were large, and little cytoplasm was contained therein. The chromatin was loose, with signs of mitosis. The tumor had few capillaries and had multiple point-shaped small foci necrosis.

It is clear that the medicament of the present invention has strong inhibitory effect on human lung cancer NCI-H460 cell.

3. The Inhibition Effect on the Growth of Human Colon Cancer COLO 205

Injectable hydroxycamptothecin (trade name: Xi Su, Wuhan Lishizhen Pharmaceuticals Inc., Huangshi Lishizhen Pharmaceuticals Group, P. R. China) was used as positive control, administered by intraperitoneal injection at the dose of 1 mg/kg, once per day. The administration was terminated after 15 consecutive days of administration. It was observed that the growth of the tumors was significant; therefore an additional one-week administration of hydroxycamptothecin was given by intraperitoneal injection at the dose of 100 mg/kg after 8 days. A single administration of 80 mg/kg hydroxycamptothecin was further given after two weeks. CPT was given to three treatment groups at the doses of 1.7 mg/kg, 5.0 mg/kg, 15.0 mg/kg respectively by intraperitoneal injection, once per day. The treatment contained a total of 15 injections.

Figures 1, 7:
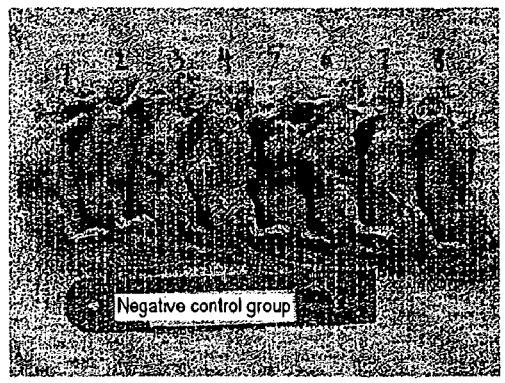
Figures 2, 7:
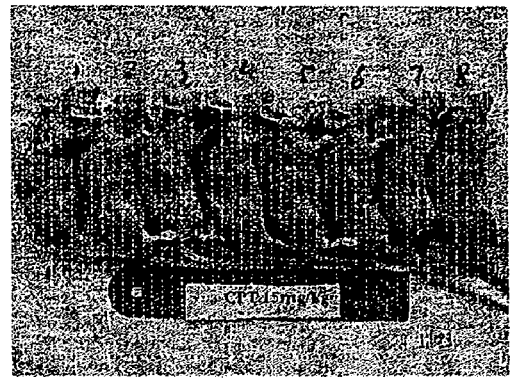
Figures 3, 7:
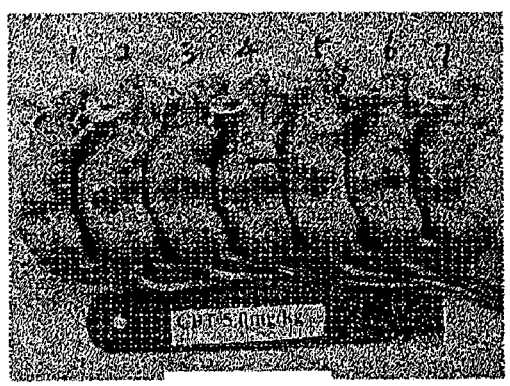
Figures 4, 7:
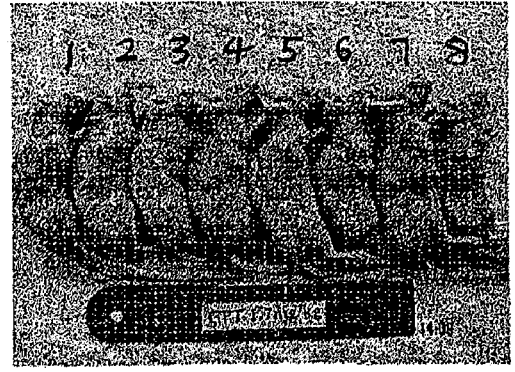
Figures 5, 7:
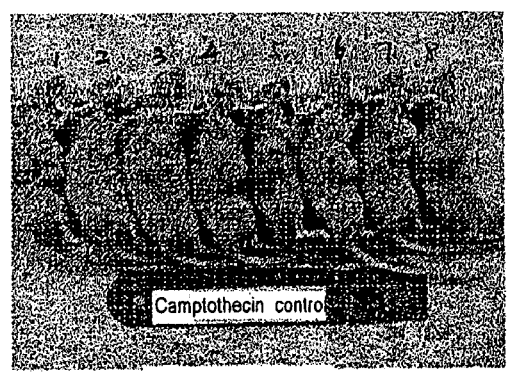

The experimental results were shown in Table 6 and 7 and FIGS. 6 and 7-1 to 7-5, wherein FIG. 7-1 is for the negative control group; FIG. 7-2 is for the group treated by 15.0 mg/kg CPT; FIG. 7-3 is for the group treated by 5.0 mg/kg CPT; FIG. 7-4 is for the group treated by 1.7 mg/kg CPT; FIG. 7-5 is for the hydroxycamptothecin positive control group. The results showed that CPT exhibited a significant inhibition effect on the growth of transplanted tumor (human colon cancer COLO 205) in nude mice. Tumors reduced in size significantly in the group treated by high-dose of CPT after five days of treatment. Some tumors even disappeared with the increase of the number of administrations. Observation on those mice was conducted for four weeks after the administration was stopped, and no tumor was found in ⅓ of the animals. Gross anatomical analysis of those mice only found some signs of inoculation beneath the skin. The inhibition rates of tumors by weight for the three treated groups were 79.6%, 90.8% and 97.4% respectively. Compared with the control group, the tumor weights of all the treated groups showed a significant or very significant statistical difference. The relative tumor growth rate T/C(%) values for all the treated groups were <60; the relative tumor volumes (RTV) were significantly different in statistics compared with that of the control group. Particularly, T/C(%) value for the group treated by high dosage of CPT was <10, indicating that CPT has a high activity on this kind of tumor.

TABLE 6

The inhibition effect of CPT on the growth of human colon cancer COLO 205

| Group | Animal number Start | Animal number End | Body Weight (g) Start | Body Weight (g) End | Tumor weight (g) | Inhibition rate (%) |
|---|---|---|---|---|---|---|
| Negative control | 8 | 8 | 19.5 ± 0.8 | 21.9 ± 1.9 | 1.96 ± 0.73 | |
| Hydroxycampto-thecin control | 8 | 8 | 20.4 ± 0.9 | 21.0 ± 2.5 | 0.66 ± 0.26** | 66.3 |
| CPT 1.7 mg/kg | 8 | 8 | 20.6 ± 1.1 | 20.6 ± 3.0 | 0.40 ± 0.33** | 79.6 |
| CPT 5.0 mg/kg | 8 | 7 | 20.2 ± 0.8 | 21.4 ± 1.2 | 0.18 ± 0.15** | 90.9 |
| CPT 15 mg/kg | 8 | 8 | 20.0 ± 0.5 | 21.1 ± 2.4 | 0.05 ± 0.05** | 97.4 |

TABLE 7

The inhibition effect of CPT on the growth of human colon cancer COLO 205

| Group | Tumor volume (mm$^3$) Start | Tumor volume (mm$^3$) End | RTV | T/C (%) |
|---|---|---|---|---|
| Negative control | 151 ± 79 | 2532 ± 1190 | 8.30 ± 5.53 | |
| Hydroxy-camptothecin control | 150 ± 34 | 845 ± 66** | 3.92 ± 1.91* | 47.2 |
| CPT 1.7 mg/kg | 205 ± 47 | 582 ± 408** | 1.62 ± 0.62** | 19.5 |
| CPT 5.0 mg/kg | 180 ± 63 | 314 ± 175** | 0.91 ± 0.35** | 11.0 |
| CPT 15 mg/kg | 192 ± 81 | 52 ± 53** | 0.33 ± 0.27** | 4.0 |

*P < 0.05
**P < 0.01 compared with the negative control

INDUSTRIAL APPLICATIONS

Tetrazolium reduction method (MTT) assay was used to determine the anti-cancer effect of the medicament. Dose-response curves were generated by plotting with the cell inhibition rates and different concentrations of medicament, and the half inhibitory concentrations ($IC_{50}$) were calculated. Observations on many human tumor cell lines prove that the CPT formulation has a very significant inhibition effect on the growth of tumor cells. CPT exerts a very significant in vitro killing activity on more than 10 tumor cells, including human lung cancer, colon cancer, breast cancer, stomach cancer, pancreas cancer, glioma, blood cell cancer, bladder cancer, prostate cancer, colorectal cancer, cervical cancer and brain tumor cells. The half inhibitory concentrations ($IC_{50}$) of CPT for U251 (human brain glioma cell), COLO 205 (human colon cancer cell), NCI-H460 (human lung cancer cell), MDA-MB-435 (human breast cancer cell) are <0.01 μg/ml. $IC_{50}$ values of CPT for HL-60 (human promyelocytic leukemia cell), MDA-MB-231 (human breast cancer cell), PC-3 (human pancreas cancer cell) and H125 (human lung cancer cell) are <0.1 μg/ml. $IC_{50}$ of CPT for RPMI 8226 (human multiple myeloma cell) is <1 μg/ml. CPT also shows some inhibition effect on the growth of SCLC (human small-cell lung cancer cell).

The in vivo experimental results show that intraperitoneal administration of CPT at a dose of 15 mg/kg/day for 10-15 consecutive days exhibited a very significant inhibition effect on the growth of tumor cells, including human colon cancer COLO 205, human lung cancer NCI-H460, human glioma U251 etceteras.

Compared with the negative control group which did not receive any medicament, CPT can significantly slow down the growth of tumors in animals, and a high dose of administration at an early stage of the growth of transplanted tumor may cause the tumor to decrease in volume or even disappear. The effect of CPT is clearly dose dependent. In addition, the efficacy is associated with the treatment course to some extent. It was observed in nude mouse models which were transplanted with human colon cancer COLO 205 that tumor sizes were still smaller that those prior to the administration even four weeks after the administration was stopped, wherein the mice received 15 consecutive injections of CPT at a dose of 15 mg/kg/day. The presence of tumors could not be confirmed at inoculation sites in ⅓ of the animals, and only signs caused by inoculation were observed during the anatomical analysis.

All the data indicated that administration of CPT showed a significant inhibition effect on the growth of transplanted human tumors in nude mice. Compared with the control group, for U251, the inhibition rates of 15 mg/kg CPT based on tumor weight were 87.5% and 87.7% respectively; for NCI-H460, the inhibition rates were 87.0% and 88.8% respectively; for COLO 205, the inhibition rates were 97.4% and 97.8% respectively, indicating a very significant difference in statistics. Three models were employed to conduct experiment in this invention. The results indicated that the relative tumor volumes (RTV) of the three animal models showed statistically significant difference from that of the negative control group, wherein the animals were continuously administered with CPT at a dose of 5.0 mg/kg for 10-15 days. The data concerning the group treated by 15 mg/kg CPT were very significantly different from those of the negative control group, wherein all the T/C (%) values are less than 25, sometimes even below 10, which indicated that CPT had a high anti-tumor activity and the experiments had good repeatability.

CPT did not exhibit any apparent side or toxic effects on animals. No substantial difference in the parameters concerning the living status of mice, such as body weight and viability of the treated groups were observed compared with those of the negative control group, except that the sizes of tumor in the treated mice were smaller. From the above, it has been demonstrated that CPT has a significant, selective inhibition effect on tumor cells, and CPT does not induce apoptosis of the cells in normal tissues. Therefore, CPT may be used as an effective and safe medicament for treating cancers. CPT is both theoretically and industrially important and has a bright future in the market.

The invention claimed is:

1. An isolated polypeptide comprising an amino acid sequence that is at least 90% identical to SEQ ID NO:2.

2. The isolated polypeptide of claim 1 comprising the amino acid sequence of SEQ ID NO:2.

3. The isolated polypeptide of claim 1 consisting of an amino acid sequence that is at least 90% identical to SEQ ID NO:2.

4. The isolated polypeptide of claim 2 consisting of the amino acid sequence of SEQ ID NO:2.

5. The isolated polypeptide of claim 2 wherein the amino acid sequence of the polypeptide differs from SEQ ID NO:2 by the addition of 15 or fewer amino acids at the N-terminus.

6. The isolated polypeptide of claim 2 wherein the amino acid sequence of the polypeptide differs from SEQ ID NO:2 by the addition of 15 or fewer amino acids at the C-terminus.

7. A composition comprising the isolated polypeptide of any of claims 1-6 and a pharmaceutically acceptable carrier.

\* \* \* \* \*